United States Patent [19]

Schimpf et al.

[11] Patent Number: 5,315,036
[45] Date of Patent: May 24, 1994

[54] PROCESS FOR THE PREPARATION OF 2-AMINOBENZENE-1,4-DISULPHONIC ACIDS AND THE NEW COMPOUND 6-CHLORO-2-AMINOBENZENE-1,4-DISULPHONIC ACID

[75] Inventors: Rolf Schimpf, Leverkusen; Walter Horstmann, Bergisch Gladbach, both of Fed. Rep. of Germany

[73] Assignee: Bayer Aktiengesellschaft, Leverkusen, Fed. Rep. of Germany

[21] Appl. No.: 15,274

[22] Filed: Feb. 8, 1993

Related U.S. Application Data

[63] Continuation of Ser. No. 815,901, Dec. 31, 1991, abandoned, which is a continuation of Ser. No. 583,188, Oct. 5, 1990, abandoned.

[30] Foreign Application Priority Data

Nov. 9, 1989 [DE] Fed. Rep. of Germany ....... 3937342

[51] Int. Cl.$^5$ .......................................... C07C 309/46
[52] U.S. Cl. .......................................... 562/58; 562/73
[58] Field of Search .................................... 562/58, 73

[56] References Cited

U.S. PATENT DOCUMENTS 2,965,675 12/1960 Novello et al. .
4,179,476 12/1979 Franz et al. .

FOREIGN PATENT DOCUMENTS 77192 4/1905 Fed. Rep. of Germany .
285488 5/1929 United Kingdom .

*Primary Examiner*—Nicky Chan
*Attorney, Agent, or Firm*—Sprung Horn Kramer & Woods

[57] ABSTRACT

The present invention relates to an improved preparation process for 2-aminobenzene-1,4-disulphonic acids and the new compound 6-chloro-2-aminobenzene-1,4-disulphonic acid.

7 Claims, No Drawings

PROCESS FOR THE PREPARATION OF 2-AMINOBENZENE-1,4-DISULPHONIC ACIDS AND THE NEW COMPOUND 6-CHLORO-2-AMINOBENZENE-1,4-DISULPHONIC ACID

This application is a continuation, of application Ser. No. 815,901, filed Dec. 31, 1991, now abandoned, which is a continuation of application Ser. No. 583,188, filed Oct. 5, 1990, now abandoned.

The present invention relates to an improved process for the preparation of 2-aminobenzene-1,4-disulphonic acids and the new compound 6-chloro-2-aminobenzene-1,4-disulphonic acid.

Various processes are known for the preparation of 2-aminobenzene-1,4-disulphonic acids. For example, aniline-3-sulphonic acid can be heated with oleum at 160° C. for 6 hours, and the resulting reaction mixture diluted with water and heated under reflux for 5 hours. On salting-out with sodium chloride, 2-aminobenzene-1,4-disulphonic acid is obtained in 90% yield (see Friedländer 16, 382). However, this process has a number of disadvantages: thus the starting material aniline-3-sulphonic acid must first be dried before it can be employed. The reaction with oleum at 160° C. requires special industrial expenditure and safety measures. The salt-containing dilute acid obtained can only be worked up with difficulty, since considerable problems occur in the recovery of sulphur dioxide owing to salt deposits.

Chlorosulphonic acid can also be employed instead of oleum (see Ber. 21, 3412 (1888)). In this case, the same disadvantages occur as with the use of oleum.

In another process for the preparation of 2-aminobenzene-1,4-disulphonic acid, 2-nitrobenzene-1,4-disulphonic acid is reduced with iron in acetic acid-containing solution (see Friedländer 4, 38). The 2-nitrobenzene-1,4-disulphonic acid required as a starting material in this case is prepared by reaction of 4-chloro-3-nitrobenzene-l-sulphonic acid with 1.2 moles of sodium sulphite in alkaline solution at a pH of 8 to 11 and temperatures of 100° C. The reworking of this process led to yields of at most 76% of theory, relative to 4-chloro-3-nitrobenzene-1-sulphonic acid employed (see Example 3). In addition to the moderate yield, this process has further disadvantages: thus the 2-nitrobenzene-1,4-disulphonic acid is salted out with sodium chloride and intermediately isolated. The solution present after the reduction with iron is obtained in great dilution and must first be concentrated up, before 2-aminobenzene-1,4-disulphonic acid can be separated off.

The reduction of 2-nitrobenzene-1,4-disulphonic acid with iron has also been described as a semi-continuous process (see DE-OS (German Published Specification) 2,534,176). In this case, a yield of 74% was achieved.

It is further known that side reactions can occur in the reaction of chloronitrobenzene-sulphonic acids with sulphites. In addition to the desired replacement of the chlorine atom by the sulpho group, the nitro group can be reduced (Piria reaction) and/or the halogen atom can be removed by hydrolysis. In the latter case, 2-aminophenol-4-sulphonic acid is formed from 4-chloro-3-nitrobenzene-1-sulphonic acid (Houben-Weyl, Methoden der organischen Chemie (Methods of Organic Chemistry), Volume 11/1 (1957), page 457).

A process has now been found for the preparation of 2-aminobenzene-1,4-disulphonic acids of the formula (I)

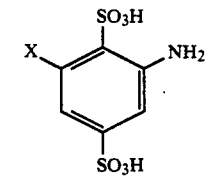

in which
x represents hydrogen or chlorine,
in which 4-chloro-3-nitrobenzene-sulphonic acids of the formula (II)

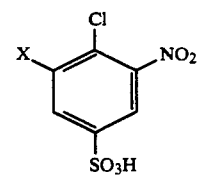

in which
x represents hydrogen or chlorine,
are reacted with sodium sulphite in an aqueous alkaline medium and then reduced with iron, which is characterized in that the reaction with sodium sulphite is carried out at 40° to 90° C., no intermediate isolation is carried out before the reduction with iron and 2-aminobenzene-1,4-disulphonic acids of the formula (I) are isolated after filtering off the iron oxide, after a PH of <1 has been established in the filtrate at 70° to 90° C. using mineral acid and after the filtrate has been cooled.

4-Chloro-3-nitrobenzene-sulphonic acid (formula (II), X=hydrogen) is a known product (see P. Fischer, Ber. 24, 3187-3188 (1891)) which is also used in the prior art processes. 4,5-Dichloro-3-nitrobenzene-sulphonic acid (formula (II), X=chlorine) can be prepared, for example, analogously to 4-chloro-3-nitrobenzene-sulphonic acid.

According to the invention, the reaction with sodium sulphite is carried out at 40° to 90° C., preferably 60° to 80° C. A procedure can be used in this case, for example, in which 1 mole of a 4-chloro-3-nitrobenzene-sulphonic acid of the formula (II) is heated at the reaction temperature with 1.0 to 1.5 moles, preferably 1.1 to 1.3 moles, of sodium sulphite or an equimolar amount of an equimolar mixture of sodium hydrogen sulphite and sodium hydroxide solution together with water at a pH of 8 to 12, preferably 10 to 11.5, for 1 to 3 hours. The essential difference from the prior art is the low reaction temperature in this process step.

In contrast to the prior art, the 2-nitrobenzene-1,4-disulphonic acid present in the reaction mixture after the first reaction step is not isolated in the process according to the invention.

The reduction with iron can be carried out, for example, by allowing the mixture obtained after the reaction with sodium sulphite, if desired after lowering the pH to 5 to 7 (for example by addition of acetic acid), to run into a mixture of water and iron which has been etched with acetic acid. Suitable temperatures for the reduction are, for example, 85° to 100° C. After completion of the reduction, the reduction mixture is rendered alkaline, for example by adding sodium carbonate, and the iron oxide formed is separated off, for example by filtration. It is advantageous to work up the filtrate obtained in this way together with the filtrate which is obtained when the iron oxide separated off is washed with warm water.

In contrast to the prior art, 2-aminobenzene-1,4-disulphonic acids of the formula (I) prepared in this way are not isolated by concentration of the combined filtrates. According to the invention, the combined filtrates are first brought to a temperature of 70° to 90° C., a pH of <1 is established using mineral acid, preferably sulphuric acid, and the mixture is then cooled, for example to 10° to 30° C. The 2-aminobenzene-1,4-disulphonic acid of the formula (I) prepared in this case precipitates in the form of crystals which can be separated off, for example by filtration.

2-Aminobenzene-1,4-disulphonic acid is an intermediate for the preparation of azo dyes (see German Patent Specifications 416,617, 450,998 and 453,133) and optical brighteners (see DE-OS (German Published Specification) 2,403,455).

It has furthermore been found that during the preparation, according to the invention, of 2-aminobenzene-1,4-disulphonic acids of the formula (I) in the reaction with sodium sulphite and in the reduction with iron new 2-N-sulphonaminobenzene-1,4-disulphonic acids are formed of the formula (III)

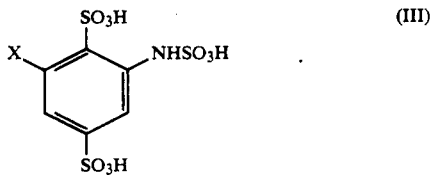

in which
x represents hydrogen or chlorine,
which, in the isolation according to the invention of the 2-aminobenzene-1,4-disulphonic acids of the formula (I), are converted into the latter and thus give a clearly higher yield. This is in general 88 to 92% of theory.

The process according to the invention is additionally distinguished by a simple procedure which requires no special safety precautions.

With respect to the prior art described at the beginning, the advantages which can be achieved using the process according to the invention are to be regarded as extremely surprising.

The present invention also relates to the new compound 6-chloro-2-aminobenzene-1,4-disulphonic acid, which corresponds to the formula (Ia)

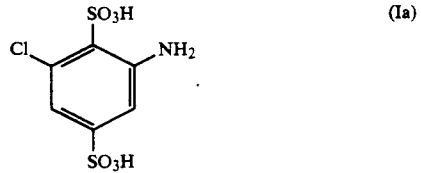

The compound of the formula (Ia) can be used as an intermediate for the preparation of azo dyes and optical brighteners.

The compounds of the formula (III) can be isolated from mixtures of 2-aminobenzene-1,4-disulphonic acid and 2-N-sulphonaminobenzene-1,4-disulphonic acid or 2-amino-6-chlorobenzene-1,4-disulphonic acid and 2-N-sulphonamino-6-chlorobenzene-1,4-disulphonic acid, as are obtained in the process according to the invention for the preparation of 2-aminobenzene-1,4-disulphonic acids of the formula (I) after the reduction with iron, for example by concentrating the filtrate present after separating off the iron, filtering off the precipitate deposited and recrystallizing several times, for example 2 to 4 times, from a methanol/water mixture. Pure products of the formula (III) can be obtained by carrying out preparative thin-layer chromatography subsequently to the recrystallizations. Investigations by means of $^1$H-NMR spectroscopy on compounds of the formula (III) isolated and purified in this manner confirm the structure given in formula (III).

EXAMPLES

Example 1

484 g of moist sodium salt of 4-chloro-3-nitrobenzenesulphonic acid (with adhering sulphuric acid and sodium hydrogen sulphate), corresponding to 1 mol, were initially introduced with 627 ml of water and the mixture was adjusted to a pH of 10.5 using 63 ml of 50% strength by weight sodium hydroxide solution. 145 g of anhydrous sodium sulphite (99% strength by weight, 1.16 mol) were then added and the reaction mixture was warmed to 60° C. After stirring at 60° C. for 1.5 hours, a PH of 6 to 7 was established by adding acetic acid. The mixture thus obtained was then added dropwise at 98° C. in the course of one hour to a mixture of 414 g of iron filings (7.4 mol), 150 ml of water and 2 ml of acetic acid. 20 minutes after completion of the addition, the reaction mixture was rendered alkaline using sodium carbonate and the iron oxide deposited was filtered off with suction. The iron oxide was then washed with 300 ml of warm water. The two filtrates were combined, warmed to 80° C. and acidified using 132 ml of 78% strength by weight sulphuric acid (1.8 mol), a pH of 0.5 resulting. After stirring at 80° C. for 30 minutes, the mixture was cooled to 20° C. with stirring and the white, coarsely crystalline 2-aminobenzene-1,4-disulphonic acid thus deposited was filtered off. 342.7 g of moist product were obtained, which corresponded to 231 g of 100% pure product with a yield of 91% of theory.

Example 2

443 g of moist sodium salt of 4,5-dichloro-3-nitrobenzene-1-sulphonic acid (with adhering sulphuric acid and sodium hydrogen sulphate), corresponding to 1 mol, were initially introduced in 400 ml of water and adjusted to a PH of 11 using concentrated sodium hydroxide solution. 299 ml of sodium hydrogen sulphite solution (containing 435 g of sodium hydrogen sulphite per liter=1.25 mol) and 66 ml of concentrated sodium hydroxide solution (1.26 mol) were then allowed to run in simultaneously so that the pH was in the range from 8 to 11 and the temperature did not exceed 35° C. The reaction mixture was then heated to 80° C. and subsequently stirred at this temperature for 30 minutes. The suspension was then neutralized to a pH in the range from 6 to 7 by adding 6 ml of acetic acid. This reaction mixture was added dropwise at 98° C. in the course of one hour to a mixture of 414 g of iron filings (7.4 mol), 150 ml of water and 2 ml of acetic acid. After completion of the addition, the reaction mixture was subsequently stirred for a further 20 minutes, then it was brought to a pH of 8 to 9 using sodium carbonate and the iron oxide deposited was filtered off with suction. The iron oxide was then washed with 300 ml of warm water and the two filtrates were combined. The combined filtrates were warmed to 80° C., acidified with 84 ml of 78% strength by weight sulphuric acid (1.14 mol), which gave a pH of 0.5, and subsequently stirred at 80° C. for a further 30 minutes. The mixture was then cooled to 20° C. with stirring and the yellowish-colored, coarsely crystalline 6-chloro-2-aminobenzene-1,4-disulphonic acid precipitated was filtered off. 352.9 g of moist product were obtained, which corresponded to 253 g of 100% pure product and a yield of 88% of theory.

The new 6-chloro-2-aminobenzo-1,4-disulphonic acid was characterized by elemental analysis and the $^1$H-NMR spectrum in NAOD as the Bolvent ($\delta$ 7.2 ppm singlet).

Example 3 (reworking of Friedländer 4, 38)

484 g of moist sodium salt of 4-chloro-3-nitrobenzene-1-sulphonic acid (with adhering sulphuric acid and sodium hydrogen sulphate), corresponding to 1 mol, were initially introduced in 650 ml of water and adjusted to a pH of 7 to 8 using 59 ml of 50% strength by weight sodium hydroxide solution. 147 g of anhydrous sodium sulphite (1.2 mol) were then added, and the reaction mixture was heated to boiling temperature and left at this temperature for 2 hours. 115 g of sodium chloride (1.97 mol) were then added, the mixture was cooled to 24° C. with stirring and the precipitate deposited was filtered off. The isolated solid was dissolved in 2,300 ml of water and this solution was added dropwise at 98° C. in the course of one hour to a mixture of 414 g of iron (7.4 mol), 150 ml of water and 2 ml of acetic acid. 20 minutes after completion of the addition, the reaction mixture was rendered alkaline with sodium carbonate and the iron oxide deposited was filtered off with suction. The iron oxide was then washed with 300 ml of warm water. The combined filtrates were warmed to 80° C., acidified with 182 ml of 78% strength by weight sulphuric acid (2.47 mol), which gave a pH of 0.5. The mixture was subsequently stirred at 80° C. for a further 30 minutes, then 1,600 ml of water were removed by distillation at 102° to 108° C. up to the start of crystallization. After cooling to 20° C. with stirring, the deposited precipitate was filtered off. 235 g of moist 2-aminobenzene-1,4-disulphonic acid were obtained in the form of pale-grey, coarse crystals. This corresponds to 192.2 g of 100% pure product and a yield of 76% of theory.

What is claimed is:

1. A Process for the preparation of an 2-aminobenzene-1,4-disulphonic acid of the formula (1)

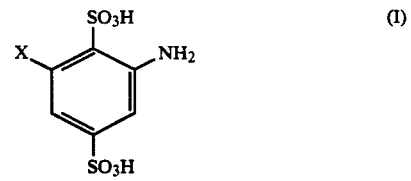

in which
X represents hydrogen or chlorine,
in which a 4-chloro-3-nitrobenzene-sulphonic acid of the formula (II)

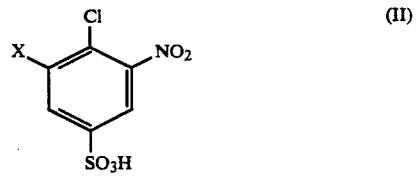

in which
X represents hydrogen or chlorine,
is reacted with sodium sulphite in an aqueous alkaline medium and then reduced with iron, in which process the reaction with sodium sulphite is carried out at 40° to 90° C., no intermediate isolation is carried out before the reduction with iron and the 2-aminobenzene-1,4-disulphonic acid of the formula (I) is isolated after filtering off the iron oxide, after a pH of <1 has been established in the filtrate at 70° to 90° C. using mineral acid and after the filtrate has been cooled.

2. The process of claim 1, in which 1.0 to 1.5 moles of sodium sulphite are employed per mole of the compound of the formula (H).

3. The process of claim 1, in which the reaction with sodium sulphite is carried out at 60° to 80 ° C.

4. The process of claim 1, in which the reaction with sodium suphite is carried out at a pH of 8 to 12.

5. The process of claim 1, in which the reduction with iron is carried out at 85 to 100° C. and at a pH in the range from 5 to 7.

6. The process of claim 1, in which sulphuiic acid is used as the mineral acid.

7. The process of claim 1, in which the filtrate is finally cooled to a temperature of 10° to 30° C.

* * * * *

UNITED STATES PATENT AND TRADEMARK OFFICE
CERTIFICATE OF CORRECTION

PATENT NO. : 5,315,036
DATED : May 24, 1994
INVENTOR(S) : Schimpf, et al.

It is certified that error appears in the above-identified patent and that said Letters Patent is hereby corrected as shown below:

Title Page, Item [63] Related U.S. Application Data: Delete Ser. No. " 583,188 " and substitute -- 593,188 --

Col. 2, line 31    Delete "PH " and substitute -- pH --

Col. 4, line 24    Delete " PH " and substitute -- pH --

Col. 4, line 49    Delete " PH " and substitute -- pH --

Col. 6, line 38    Delete " formula (H) " and substitute -- formula (II) --

Col. 6, line 46    Delete " sulphuiis " and substitute -- sulphuric --

Signed and Sealed this

Sixth Day of September, 1994

*Attest:*

BRUCE LEHMAN

*Attesting Officer*    *Commissioner of Patents and Trademarks*